US00PP23410P2

(12) United States Plant Patent
Uebelhart

(10) Patent No.: US PP23,410 P2
(45) Date of Patent: Feb. 19, 2013

(54) ***HELIOPSIS* PLANT NAMED 'SUMMER GREEN'**

(50) Latin Name: ***Heliopsis helianthoides* var. *scabra***
Varietal Denomination: Summer Green

(75) Inventor: Georg G. Uebelhart, Schwarmstedt (DE)

(73) Assignee: Jelitto Staudensamen GmbH, Schwarmstedt (DE)

( * ) Notice: Subject to any disclaimer, the term of this patent is extended or adjusted under 35 U.S.C. 154(b) by 101 days.

(21) Appl. No.: 13/065,162

(22) Filed: Mar. 15, 2011

(51) Int. Cl.
*A01H 5/00* (2006.01)

(52) U.S. Cl. ..... Plt./437

(58) Field of Classification Search ..... Plt./437
See application file for complete search history.

(56) References Cited

PUBLICATIONS

Darwin Plants—Perennials 2012. Retrieved on Aug. 2, 2012. Retrieved from the Internet at <www.darwinplants.com/site/genus.asp?GenusId=Heliopsis> 2 pp.*

* cited by examiner

*Primary Examiner* — June Hwu
(74) *Attorney, Agent, or Firm* — Penny J. Aguirre

(57) ABSTRACT

A new cultivar of *Heliopsis*, 'Summer Green', characterized by its inflorescences with yellow ray florets and red cones, its slightly curled foliage that is variegated with blades that are light green to creamy white in color with dark green veins, its stems that are dark reddish in color, and its ability to bloom predictably as a one-year-old plant.

2 Drawing Sheets

Botanical classification: *Heliopsis helianthoides* var. *scabra*.

Variety denomination: 'Summer Green'.

CROSS REFERENCE TO A RELATED APPLICATION

This application is co-pending with a U.S. Plant Patent Applications filed for plants derived from the same cross in the Inventor's breeding program that are entitled *Heliopsis* Plant Named 'Summer Pink' (U.S. Plant patent application Ser. No. 13/065,161), and *Heliopsis* Plant Named 'Summer Stripe' (U.S. Plant patent application Ser. No. 13/065,117).

BACKGROUND OF THE INVENTION

The present invention relates to a new and distinct cultivar of *Heliopsis* plant, botanically known as *Heliopsis helianthoides* var. *scabra* 'Summer Green' and will be referred to hereinafter by its cultivar name, 'Summer Green'.

'Summer Green' was derived from a controlled breeding program conducted by the Inventor in a nursery in Schwarmstedt, Germany. The breeding program focuses on obtaining new cultivars of *Heliopsis* with novel leaf, stem, and flower colors and superior garden performance. 'Summer Green' was selected in 2007 by the Inventor as a single unique plant derived in 2005 from a cross made between unnamed plants from his breeding program with the female parent identified with accession No. H04011 and the male parent identified with accession No. GU03.

Asexual reproduction of the new cultivar was first accomplished via stem cuttings under the direction of the Inventor in Lisse, the Netherlands in summer of 2008. Propagation by stem cutting and tissue culture has determined that the characteristics of this cultivar are stable and are reproduced true to type in successive generations.

SUMMARY OF THE INVENTION

The following traits have been repeatedly observed and are determined to be the characteristics of the new cultivar of *Heliopsis*. These attributes in combination distinguish 'Summer Green' as unique from and all other cultivars of *Heliopsis* known to the Inventor.

1. 'Summer Green' exhibits inflorescences with yellow ray florets and red cones when mature.
2. 'Summer Green' exhibits slightly curled foliage that is variegated with blades that are light green to creamy white in color with dark green veins.
3. 'Summer Green' exhibits stems that are dark reddish in color.
4. 'Summer Green' blooms predictably as a one-year-old plant.

'Summer Green' can be compared to its parents. The female parent is similar to 'Summer Green' in having reddish stems but differs from 'Summer Green' in having purplish green foliage without variegation. The male parent is similar to 'Summer Green' in having variegated foliage but differs from 'Summer Green' in lacking reddish stems. 'Summer Green' can also be compared to *Heliopsis* cultivar 'Loraine Sunshine' (U.S. Plant Pat. No. 10,690). 'Loraine Sunshine' is similar to 'Summer Green' in having variegated foliage but differs from 'Summer Green' in having green stems, inflorescences with a yellow cone, and in being less predictable in flowering as a one year-old plant. 'Summer Green' can also be compared to cultivars from the same cross; 'Summer Stripe' and 'Summer Pink'. 'Summer Stripe' differs from 'Summer Green' in having foliage that is variegated with white and pink with green veins. 'Summer Pink' differs from 'Summer Green' in having inflorescence with orange coloration at the base of the ray florets and in having variegated foliage that is green to creamy white and pink with green veins.

BRIEF DESCRIPTION OF THE DRAWINGS

The accompanying colored photographs illustrate the overall appearance and distinct characteristics of the new *Heliopsis*. The photographs were taken of a one year-old plant as grown in a 3.5-liter container in a cold-story greenhouse in Lisse, the Netherlands.

The photograph in FIG. 1 provides a side view of a plant of 'Summer Green' in bloom.

Figure 1:
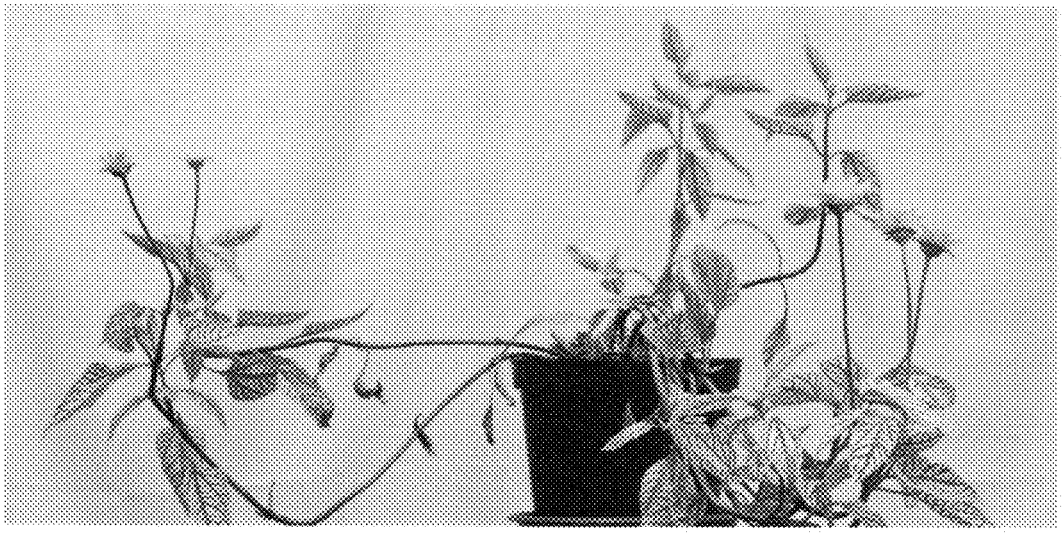
Figure 2:
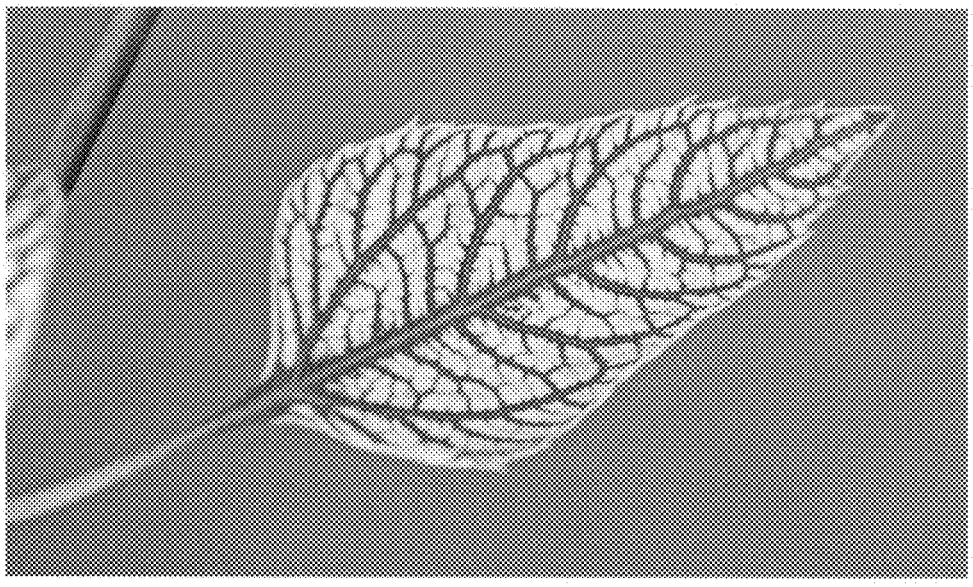

The photograph in FIG. 2 provides a close-up view of the upper surface of a leaf of 'Summer Green'.

Figure 3:
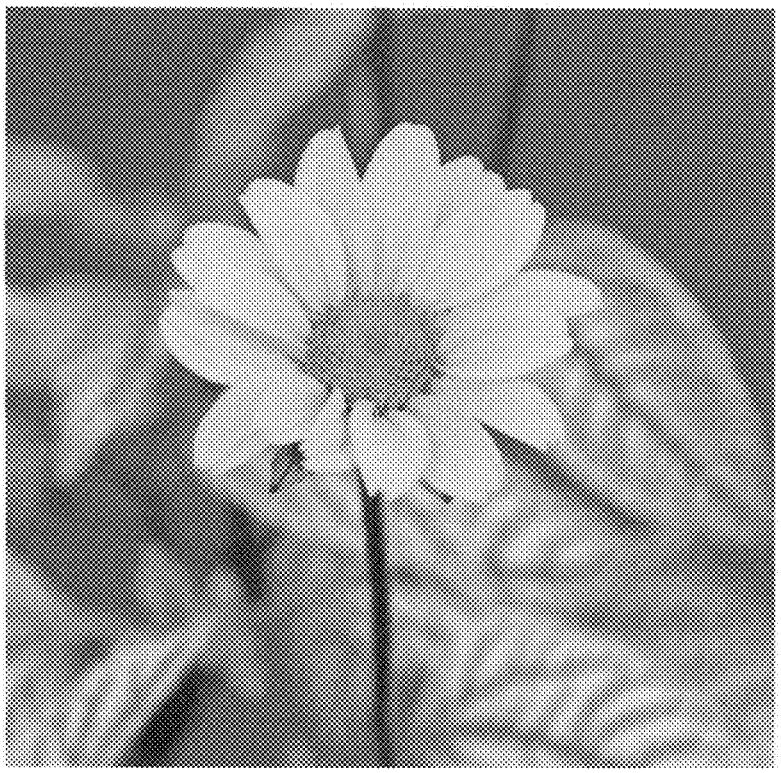

The photograph in FIG. 3 provides a close-up view of an inflorescence of 'Summer Green'.

The colors in the photographs are as close as possible with the digital photography and printing techniques utilized and the color codes in the detailed botanical description more accurately describe the colors of the new *Heliopsis*.

DETAILED BOTANICAL DESCRIPTION

The following is a detailed description of the new cultivar collected in June from one year-old plants as grown in 3.5 liter containers in cold-storey greenhouses in Lisse, The Netherlands with day temperatures ranging between 18° to 30° C. and night temperatures ranging between 8° and 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming season.*—July to September in Germany.

*Plant habit.*—Herbaceous perennial, upright, clumping growth habit.

*Height and spread.*—About 120 cm in height and 60 cm in spread after 2 years.

*Hardiness.*—U.S.D A. Zones 3 to 9.

*Diseases resistance.*—No susceptibility or resistance to diseases has been observed.

*Stress resistance.*—Moderate resistance to rain, high resistance to wind.

*Root description.*—Fibrous.

Growth and propagation:

*Propagation.*—Stem cuttings and tissue culture.

*Time from stem cutting to flowering.*—Average of 20 weeks.

*Crop maintenance.*—No pinching or pruning required.

*Growth rate.*—Vigorous, but slower growing in comparison to cultivars with green foliage.

Stem description:

*Stem shape.*—Rounded.

*Stem aspect.*—Average 30° from vertical.

*Stem strength.*—Moderate.

*Stem color.*—A blend of 197A and N199A and 187A.

*Stem surface.*—Young stems slightly pubescent, hairs 1 mm in length, 157D in color, deciduous, mature stems glossy, and glabrous.

*Lateral branch length.*—Average of 43.9 cm.

*Lateral branch diameter.*—Average of 2 mm.

*Quantity of lateral branches.*—About 15 per plant.

*Internode length.*—Average of 6.9 cm.

*Branching.*—Moderately branched.

Foliage description:

*Leaf division.*—Simple.

*Leaf shape.*—Ovate-lanceolate, strongly concave.

*Leaf base.*—Attenuate.

*Leaf apex.*—Acute.

*Leaf margin.*—Serrate.

*Leaf venation.*—Pinnate, upper surface 147C, lower surface a blend of 146C and 146D.

*Leaf attachment.*—Petiolate.

*Leaf arrangement.*—Opposite.

*Leaf surface.*—Upper and lower surfaces dull and moderately strigose with strigose hairs and 0.2 mm in length.

*Leaf color.*—Young foliage upper surface; a blend of 154C and 154D to 2D with pinnate veins 147C and reticulate veins 143B to 143C, young foliage lower surface; 154D with pinnate veins a blend of 146C and 146D and reticulate veins 143C, mature foliage upper surface; ranging from 150D to 2D with areas a blend of 146C and 146D, pinnate veins 147C and reticulate veins N137A, mature foliage lower surface; 154D with pinnate veins a blend of 146C and 146D and reticulate veins 137C.

*Leaf size.*—Average of 7.6 cm in length and 3.8 cm in width.

*Petiole.*—Smooth, average of 2.1 cm in length and 1.8 mm in diameter, upper surface; moderately glossy, 147C in color, lower surface; very glossy, 146B in color.

Flower description:

General description:

*Inflorescence type.*—Terminal capitulum with many disc florets, one row of ray florets, and two rows of involucral bracts.

*Flowering response.*—9 weeks.

*Rate of flowering.*—Staggered starting from the terminal inflorescence towards the youngest lateral inflorescence.

*Lastingness of inflorescence.*—About 5 weeks, persistent.

*Fragrance.*—None.

*Quantity of inflorescences.*—1 per lateral stem, 20 per plant.

*Inflorescence buds.*—About 1 cm in depth and 2.1 cm in diameter, flattened globular in shape, a blend of 144B and 144C in color.

*Inflorescence size.*—About 1.9 cm in depth and 4.4 cm in diameter, diameter of disk about 1.4 cm, height of disk about 1.7 cm.

*Receptacle.*—Rhomboidal, about 6 mm in depth and 4 mm in diameter, 155C in color.

*Peduncle.*—Round with axial ribs, moderately strong, N199A suffused with 148A, about 14.3 cm in length, 2 mm in diameter, surface is slightly pubescent. Involucral bracts (phyllaries). — Oblong in shape, 14 per inflorescence, arranged in 2 rows, broadly acute apex, broadly cuneate base, margin entire, upper surface 143A in color, lower surface 143C in color, about 1.1 mm in length, 5 mm in width, surface is dull and moderately strigose with hairs about 0.2 to 0.5 mm in length and 157D in color on upper and lower surface.

Ray florets (capitulate):

*Number.*—Average of 14.

*Arrangement.*—Rotate.

*Appearance.*—Smooth, dull.
*Shape.*—Elliptic.
*Aspect.*—Slightly upright at an angle of 10° from horizontal.
*Size.*—Average of 2 cm in length and 9 mm in width.
*Petal apex.*—Emarginate to praemorse.
*Petal base.*—Cuneate.
*Petal margins.*—Entire.
*Petal texture.*—Smooth, slightly ribbed lengthwise.
*Petal color.*—Opening; upper surface 7A, lower surface a blend of 1A and 1B, margins a blend of 6B and 7B, fully open; upper surface 14B, lower surface 7A, color not fading.

Disk florets (perfect):
*Quantity.*—Average of 100.
*Shape.*—Tubular, sympetalous with 5 lobes comprising upper 12.5% of floret.
*Arrangement.*—Spiral concentric towards center of disc.
*Disk lobe apex.*—Acute.
*Disk lobe margin.*—Entire.
*Petal base.*—Fused.
*Petal texture.*—Smooth, dull.
*Size.*—About 9 mm in length and 2 mm in width.
*Color.*—Bud; base 145C, mid-section 148A, apex 144C, opening; base 145C, mid-section 154C, apex 1A, fully opened; base 145D, mid-section 152D, apex 53A.

Reproductive organs:
*Presence.*—Disk flowers are perfect, ray flowers are carpellate.
*Gynoecium.*—1 pistil per disk and ray floret, 7 mm in length, stigma decurrent and 22A in color, style 5 mm in length and a blend of 150B and 150C in color, ovary 145D in color.
*Androecium.*—5 stamen per disk floret, filament 2.5 mm in length and 145D in color, anther linear in shape, 3 mm in length, and a blend of 203A and 203B in color, pollen moderate to abundant in quantity and 17B in color.
*Fruit and seed.*—No fruits or seeds observed to date.

It is claimed:

1. A new and distinct cultivar of *Heliopsis* plant named 'Summer Green' as herein illustrated and described.

* * * * *